United States Patent [19]

Falco

[11] Patent Number: 5,500,958
[45] Date of Patent: Mar. 26, 1996

[54] SEAL PLATE ATTACHMENT FOR EARMUFFS

[75] Inventor: Robert N. Falco, Indianapolis, Ind.

[73] Assignee: Cabot Safety Corporation, Southbridge, Mass.

[21] Appl. No.: 183,559

[22] Filed: Jan. 19, 1994

[51] Int. Cl.⁶ ..................................................... A42B 1/06
[52] U.S. Cl. .................................. 2/209; 403/331
[58] Field of Search .................................. 2/2, 208, 209, 2/423; 128/864, 866, 867; 181/128, 129; 24/459, 702; 220/345, 346; 403/331

[56] References Cited

U.S. PATENT DOCUMENTS

| | | | |
|---|---|---|---|
| D. 276,855 | 12/1984 | Falco | D2/259 |
| 306,290 | 10/1884 | Sherman | 220/345 |
| 2,469,254 | 5/1949 | Bankson | 181/25 |
| 2,883,672 | 4/1959 | Hornickel et al. | 2/209 |
| 3,797,045 | 3/1974 | Aho | 2/209 |
| 3,805,298 | 4/1974 | Aho | 2/209 |
| 3,875,592 | 4/1975 | Aileo | 2/209 |
| 3,908,200 | 9/1975 | Lundin | 2/209 |
| 3,938,614 | 2/1976 | Ahs | 181/129 |
| 4,057,856 | 11/1977 | Aho | 2/209 |
| 4,158,087 | 6/1979 | Wood | 521/137 |
| 4,342,403 | 8/1982 | Badtke et al. | 220/345 |
| 4,471,496 | 9/1984 | Gardner, Jr. | 2/209 |
| 4,674,134 | 6/1987 | Lundin | 2/209 |
| 5,023,955 | 6/1991 | Murphy, II et al. | 2/209 |
| 5,144,678 | 9/1992 | Lenz | 381/183 |

FOREIGN PATENT DOCUMENTS

| | | |
|---|---|---|
| 2552320 | 3/1985 | France . |
| 8801284 | 7/1988 | Germany . |
| 840184 | 2/1958 | United Kingdom ............. 220/345 |
| 1303612 | 2/1973 | United Kingdom . |
| 1378294 | 12/1974 | United Kingdom . |
| 1508101 | 4/1978 | United Kingdom ............. 2/209 |

*Primary Examiner*—Diana Biefeld
*Attorney, Agent, or Firm*—Fishman, Dionne & Cantor

[57] ABSTRACT

A seal plate attachment for earmuffs. The seal plate attachment has a first and second portion including substantially flat surfaces, outer perimeters, and inner perimeters defining central openings. The first portion of the seal plate attachment includes a first channel extending around a section of the outer perimeter. The seal plate attachment second portion includes a rim, projecting inwardly from and extending around a section of the outer perimeter. The rim of the seal plate attachment second portion forms a second channel to oppose the first channel on the seal plate attachment first portion, allowing the second portion to be slidable relative to the first portion. An improved earmuff design includes rigid earcup elements, a connecting band, and soft sealing elements in combination with the seal plate attachments for earmuffs.

22 Claims, 3 Drawing Sheets

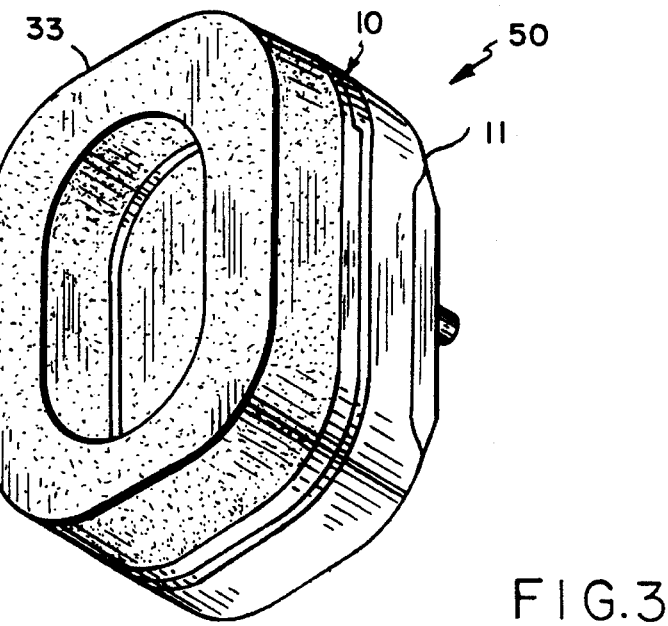
FIG. 3
FIG. 6B
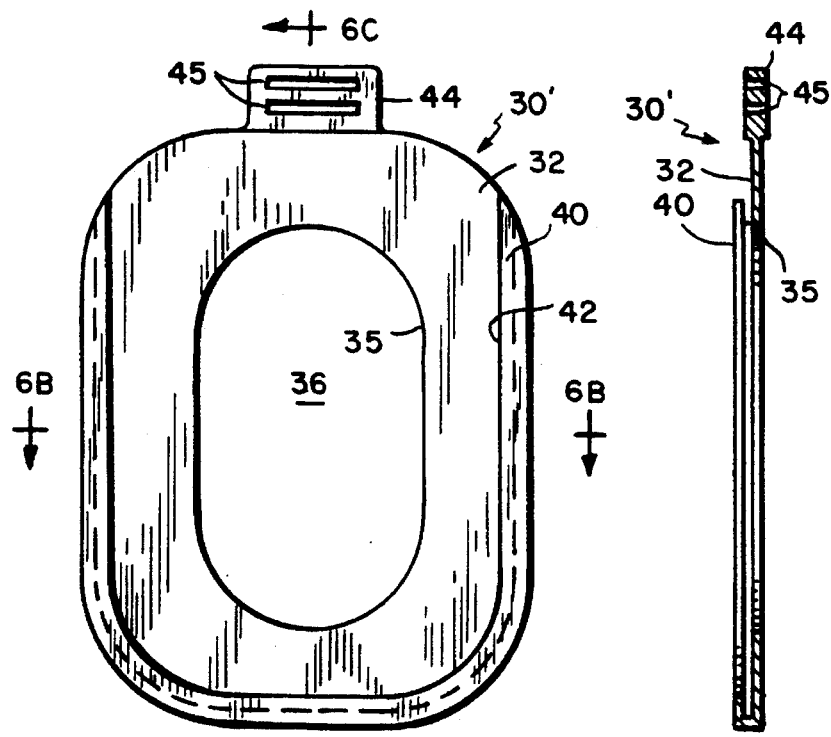
FIG. 6A
FIG. 6C

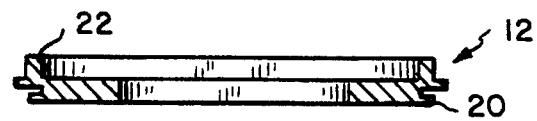
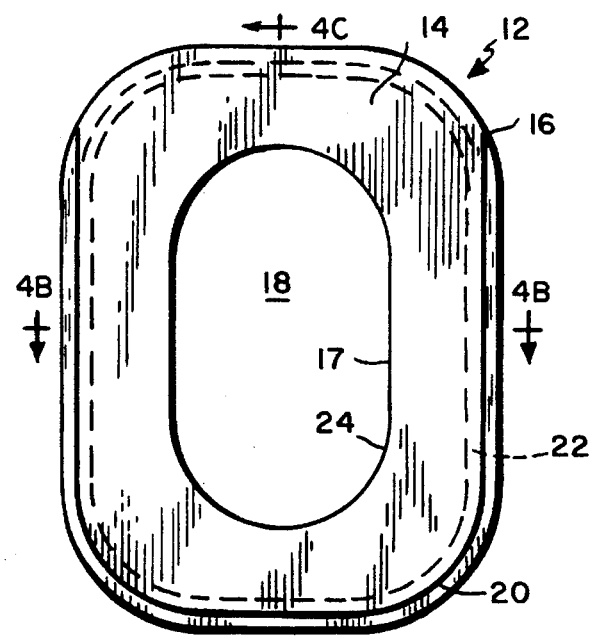
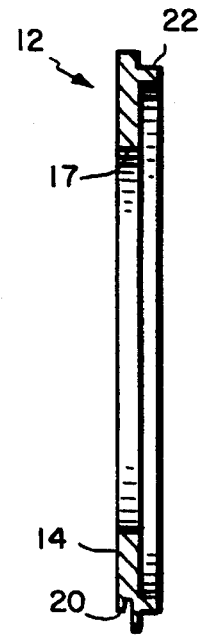
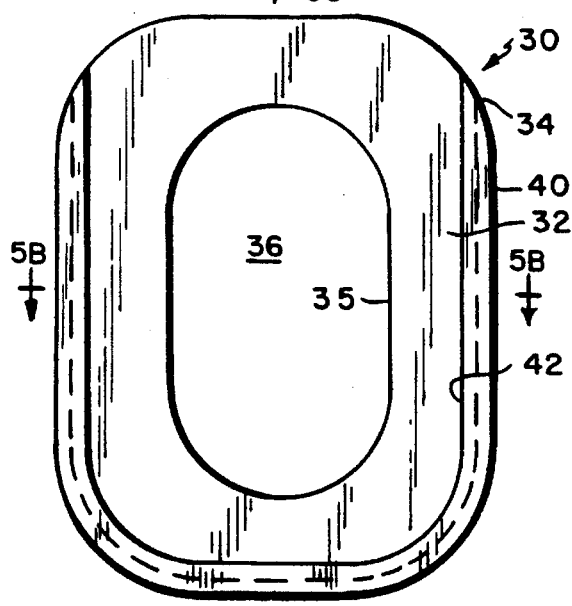
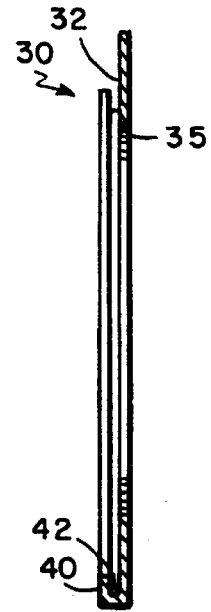

SEAL PLATE ATTACHMENT FOR EARMUFFS

BACKGROUND OF THE INVENTION

1. Field of the Invention

The present invention relates to a seal plate attachment and, more particularly, to a seal plate attachment for acoustic earmuffs.

2. Description of the Prior Art

Many types of earmuffs are available to provide users with varying degrees of noise attenuation and comfort, as required for various industrial, commercial and recreational activities. Generally, due to the expense of providing earmuffs for each user in each environment, a single pair of earmuffs may be shared by different users and/or are used in all environments. For example, industrial shift operators often use the same pair of earmuffs from one shift to the next, thereby potentially transferring contaminants. In addition, due to the user's differing head sizes and shapes, the effectiveness of an earmuff may differ from person to person. Even in situations where individual earmuffs are available to users/operators, additional problems may occur when single operators use the same earmuffs for extended periods in varying environments. When used in this manner, earmuffs can be ineffective if improper earmuff-to-head seals exists as a result of dirty or worn sealing elements, or by using earmuffs having inadequate noise attenuation for a particular situation.

To address the above noted deficiencies, the safety industry has provided various improvements to earmuff constructions. For example, an articulated earmuff-to-headband attachment construction has been disclosed in Gardner, Jr. et al., U.S. Pat. No. 4,471,966. In addition, various improvements have been suggested with respect to the soft sealing element portion of an earmuff. For example, an earmuff having a sealing ring which includes liquid and foam plastic layers is disclosed by Lundin, U.S. Pat. No. 4,674,134.

Although providing additional comfort and conformance to the head shape of any user to effectuate competent sealing of the earmuffs to the user's head, none of the foregoing, or similar earmuffs, provide an interchangeable, interlocking, light-weight and stylish earmuff. For acoustical earmuffs, varying degrees of comfort and noise attenuation are necessary for different users in different environments.

SUMMARY OF THE INVENTION

Accordingly, the present invention provides a seal plate attachment for earmuffs. The seal plate attachment includes a first and second portion having substantially flat surfaces, outer perimeters, and inner perimeters defining central openings. The first portion includes a first channel extending around a section of the outer perimeter. The seal plate attachment second portion includes a rim, which projects inwardly from and extends around a section of the outer perimeter. The rim forms a second channel to oppose the first channel, allowing the second portion to be slidable relative to the first portion. The first portion of the seal plate attachment of the present invention can be demountably attached to an earmuff cup or made integral with an earmuff cup.

The seal plate attachment of the present invention can be incorporated into an earmuff design, including rigid earcup elements, a connecting band, and soft sealing elements to provide an improved earmuff, allowing for alternative earmuff assemblies for one or many users.

The present invention therefore provides an alternative attachment for earmuffs, particularly a seal plate attachment which provides users with a simple earmuff design that can be used by different users and/or in different environments. A further object of this invention is to provide a seal plate attachment for earmuffs which can be simply and inexpensively produced while providing the user with easy interchangeability of the sealing cushion element of an earmuff, and a secure fit to ensure user safety. It is also an object of this invention to provide an improved earmuff incorporating a hygienic seal plate attachment with a rigid earcup element and a soft sealing element.

BRIEF DESCRIPTION OF THE DRAWINGS

The foregoing and other objects and advantages of the invention will be appreciated more fully from the following drawings in which:

FIG. 3 is a front perspective view of the earmuff cup and seal plate attachment, as shown in FIGS. 1 and 2, assembled.

FIG. 4A is a front view of the first portion of the seal plate attachment according to the present invention.

FIG. 4B is a cross-sectional side view of the first portion of the seal plate attachment, taken along line 4B—4B of FIG. 4A.

FIG. 4C is a cross-sectional side view, taken along line 4C—4C of FIG. 4A.

FIG. 5A is a front view of the second portion of the seal plate attachment according to the present invention.

FIG. 5B is a cross-sectional side view of the second portion of the seal plate attachment, taken along line 5B—5B of FIG. 5A.

FIG. 5C is a cross-sectional side view, taken along line 5C—5C of FIG. 5A.

FIG. 6A is a front view of an alternative embodiment of the second portion of the seal plate attachment according to the present invention.

FIG. 6B is a cross-sectional side view of the second portion of the seal plate attachment, taken along line 6B—6B of FIG. 6A.

FIG. 6C is a cross-sectional side view, taken along line 6C—6C of FIG. 6A.

DETAILED DESCRIPTION OF THE INVENTION

The seal plate attachment for earmuffs of the present invention, preferably includes a first and second portion having substantially flat surfaces, outer perimeters, and inner perimeters defining central openings. The first portion includes a first channel extending around a section of the outer perimeter. The second portion includes a rim projecting inwardly from and extending around a section of the outer perimeter. The rim of the second portion forms a second channel to oppose the first channel, allowing the second portion to be slidable relative to the first portion.

Figure 1:
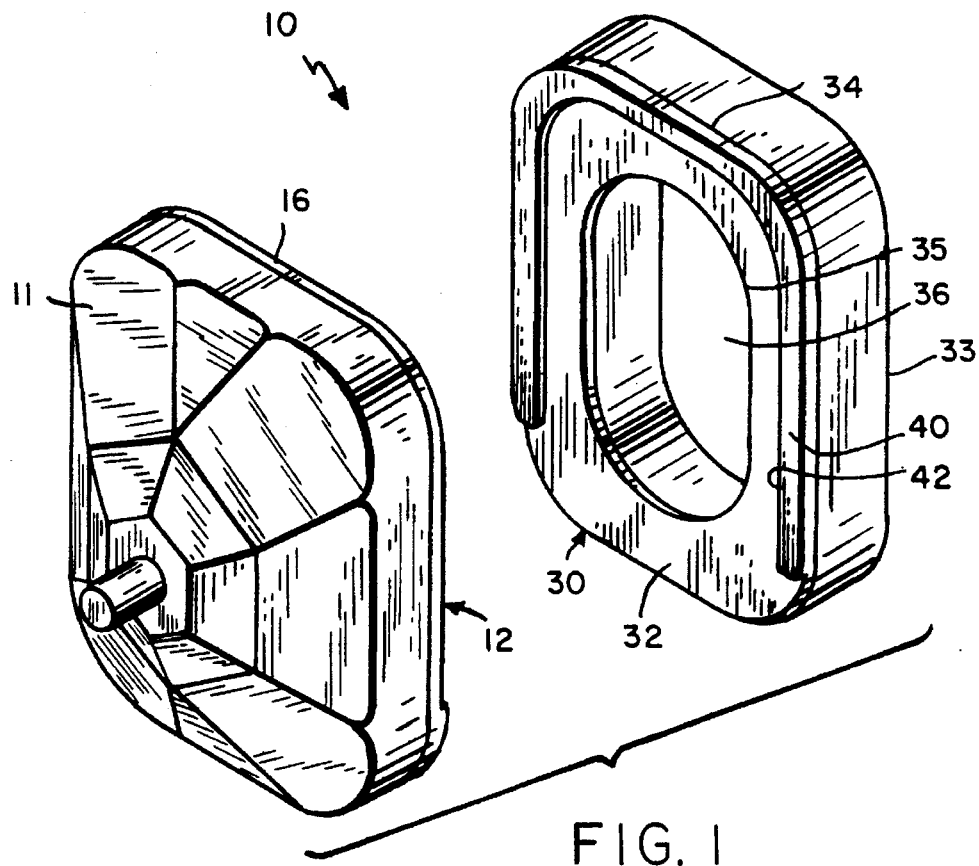
FIG. 1 is a rear perspective view of an earmuff cup and seal plate attachment of the present invention with a soft sealing element attached thereto.
Figure 2:
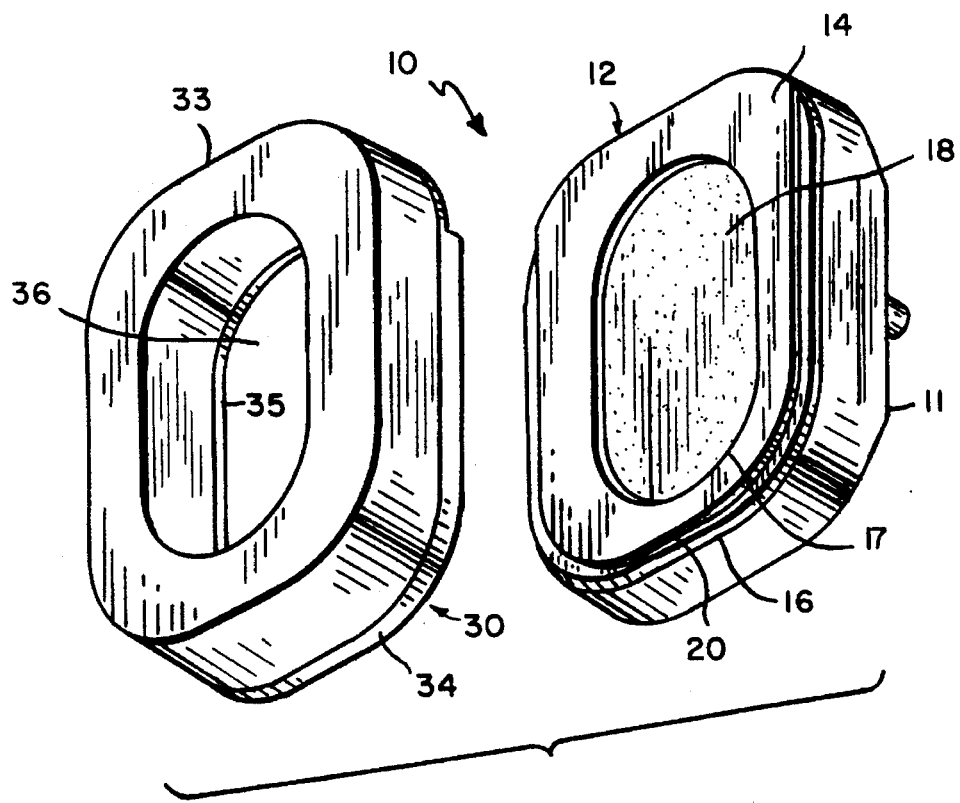
FIG. 2 is a front perspective view of the earmuff cup and seal plate attachment shown in FIG. 1.

Referring to FIGS. 1–3, seal plate attachment 10 of the present invention is shown in various stages of assembly. FIGS. 1 and 2 show rear and front perspective views of a rigid earcup element 11 incorporating seal plate attachment 10. A first portion 12 is provided having a substantially flat surface 14, an outer perimeter 16 and an inner perimeter 17 defining a central opening 18. The first portion 12 includes a first channel 20 extending around a section of the outer perimeter 16. Seal plate attachment 10 further includes a second portion 30 having a flat surface (not shown) which is covered by soft sealing element 33. Second portion 30 also includes an outer perimeter 34 and an inner perimeter 35 defining a central opening 36. A rim 40 is provided, projecting inwardly from and extending around a section of outer perimeter 34. The rim 40 forms a second channel 42, to oppose first channel 20, such that second portion 30 is slidable relative to first portion 12.

FIG. 3 shows a front perspective view of an earmuff cup 50, incorporating seal plate attachment 10 assembled, as well as rigid earcup element 11 and soft sealing element 33. Typically, a pair of earmuffs includes two earmuff cups 50 connected by a head or connecting band (not shown), which is attached to the rear portion of each earmuff cup.

Referring now to FIGS. 4A, 4B and 4C, first portion 12 is shown in detail. First portion 12 includes a substantially flat surface 14, an outer perimeter 16, and an inner perimeter 17 defining a central opening 18. First portion 12 further includes a first channel 20 which extends around a section of outer perimeter 16.

First portion 12 may be demountably attached to an earmuff cup (11, as shown in FIGS. 1–3). Typically, first portion 12 is provided with a projection 22, or the like, on the side opposite the first portion's substantially flat surface 14. Projection 22 allows first portion 12 to be snapped, or otherwise secured, into an earmuff cup. Projection 22 can be provided in a variety of sizes and shapes. For example, projection 22 may be set-in from, or extend around, outer perimeter 16. In addition, projection 22 can be comprised of a series of smaller projections, or it can be a single continuous projection, parallel to outer perimeter 16. Preferably, projection 22 is continuous and parallel to outer perimeter 16, and is set-in from the outer perimeter a distance equivalent to the thickness of the rim of an earmuff cup. A flush fit between outer perimeter 16 and the outer surface of the earmuff cup is thereby provided. Furthermore, the outer perimeter of projection 22 is preferably approximately equal in size and shape to that of the inner perimeter of the earmuff cup. Projection 22 is therefore positioned to ensure a tight fit, wherein the outer surface of the earmuff cup and outer perimeter 16 are flush when first portion 12 is secured into the earmuff cup. Alternatively, first portion 12 can be rigidly mounted to an earmuff cup by methods known to those skilled in the art, such as adhesive or ultrasonic bonding or welding. In another embodiment, first portion 12 can be formed as part of an earmuff cup by methods known to those skilled in the art, such as injection molding.

In a preferred embodiment, first portion 12 has a slightly outwardly tapered surface from inner perimeter 17 toward outer perimeter 16. This slight taper 24, which extends around inner perimeter 17 adjacent to central opening 18, is provided on first portion 12 to create a positive pressure area around inner perimeter 17. This positive pressure area of taper 24, while providing some resistance when sliding first portion 12 and second portion 30 together, will create clearance for dust and the like between the two portions. Taper 24 will also aid in establishing an acoustical seal while maintaining the assembled positions of first and second portions, 12 and 30, respectively, under normal use conditions. Taper 24 acts, in effect, as a Belleville spring or washer by distributing the stresses applied to first portion 12. While the theory of Belleville springs is complex, they have gained wide acceptance in a variety of applications. (See, for example, U. Hindhede et al., Machine Design Fundamentals 201–203.) It has been found that a 1° to 2° interface between inner perimeter 17 and outer perimeter 16 is suitable to create and maintain an acoustical seal and hold first and second portions securely in place when assembled.

Typically, first portion 12 includes a first channel 20, which extends around a section of outer perimeter 16. Preferably, first channel 20 extends around at least 50% of the first portion outer perimeter 16, to ensure that second portion 30 can slide over first portion 12 and entirely cover substantially flat surface 14 such that outer perimeters 16 and 34 are flush when seal plate attachment 10 is assembled.

First portion 12 may be constructed of a rigid or semi-rigid material. Preferably, first portion 12 is constructed of a rigid or semi-rigid plastic material or the like due to its relative inexpensive cost, lightweight, moldability and shock resistance. Most preferably, first portion 12 is constructed of a durable high-impact resistant, thermoplastic, high density material selected from the group consisting of high-density polyethylene, acrylonitrile-butadiene-styrene resin, polypropylene, polycarbonate, polyvinyl chloride, nylon, and the like. First portion 12 may be injection molded, machined, or produced by other methods known to those of skill in the art. Preferably, first portion 12 is injection molded due to the relative low processing costs.

Referring now to FIGS. 5A, 5B and 5C, second portion 30 is shown in detail. Second portion 30 includes a substantially flat surface 32, an outer perimeter 34, and an inner perimeter 35 defining a central opening 36. Second portion 30 further includes a rim 40, projecting inwardly from and extending around a section of the outer perimeter 34. Rim 40 forms a second channel 42 to oppose first channel 20, such that second portion 30 is slidable relative to first portion 12.

Second portion 30 and first portion 12 are substantially the same size and shape. Furthermore, as noted above, first channel 20 and second channel 42 extend around substantially equivalent outer perimeter sections (16 and 34, respectively) of the first and second portions. Preferably, second channel 42 extends around at least 50% of the second portion outer perimeter 34 to ensure that second portion 30 can slide over first portion 12 and entirely cover substantially flat surface 14 such that outer perimeters, 16 and 34, are flush when seal plate attachment 10 is assembled.

Second portion 30 includes a flat surface 32 whereupon a soft sealing element 33 (as shown in FIGS. 1–3) is attached. Soft sealing element 33 should be lightweight, deform readily to the head contour, distribute clamping pressure evenly over the contact area, and maintain a substantially airtight seal even under conditions of rapid movement between the head and ear enclosure. In view of the foregoing, the soft sealing element is preferably composed of a polymeric foam material such as natural rubber, polyvinyl chloride, silicon rubber, EDPM rubber, polyisobutylene, polyethylene, polyamide, polyurethane, SBR rubber, polybutadiene, ethylene vinyl acetate elastomer, acrylic elastomer, neoprene rubber, and the like. The particular polymeric foam material employed in the fabrication of the soft sealing element will obviously be dictated by consideration of economics, the specific mode of fabrication used, allergenicity and similar non-critical considerations. A preferred material is a hydrophobic polyurethane foam having a fine cell structure and high flow resistance, such as the polyurethane foam compositions disclosed by Wood in U.S. Pat. No. 4,158,087, the disclosure of which is incorporated herein by reference.

Polyurethane foams are generally preferred for their formulation flexibility, easy molding characteristics and economics. Especially preferred are polyether polyurethane foam compositions due to their softness. These foams, which tend to contribute to the sense of comfort enjoyed by the wearer, are typically derived from a polyoxyalkylene urethane prepolymer containing an aqueous synthetic polymer latex such as styrene butadiene or acrylic latex. Such prepolymers are readily water blown to form a stable foam body in a suitable mold.

Also preferred is a foam material having a low static stiffness and a high dynamic stiffness to yield a cushion with high attenuation characteristics. These stiffness characteristics can be defined in terms of dynamic complex spring constant ($k^*$), static spring constant (Ls) and dynamic material loss factor ($\eta$). Such materials are further described in U.S. Ser. No. 08/048,722, filed on Apr. 15, 1993 to Gardner, Jr. and entitled "Acoustical Earmuff," a complete copy of which is herein incorporated in its entirety by reference.

The soft sealing element 33 and second portion 30 are also substantially the same size and shape with respect to outer and inner perimeters, 34 and 35. The soft sealing element may be attached to the substantially flat surface 32 of second portion 30 by methods known to those of skill in the art, such as by a suitable adhesive.

Second portion 30 may be constructed of any flexible or semi-rigid material which is capable of providing support to soft sealing element 33. Preferably, second portion 30 is constructed of a flexible or semi-rigid plastic material, or the like, due to relatively inexpensive cost, lightweight, moldability, and shock resistance. Most preferably, second portion 30 is constructed of a thin and flexible thermoplastic to conform to, and provide a tight seal with, first portion 12 as noted above. The thin, flexible thermoplastic material used to construct second portion 30 can be selected from the group consisting of polyvinyl chloride, nylon, polypropylene, polystyrene, low-density polyethylene, and the like. Similarly to first portion 12, second portion 30 may be injection molded, machined, or produced by other methods known to those of skill in the art. Preferably, second portion 30 is also injection molded due to the relative low processing costs.

Referring now to FIGS. 6A, 6B, and 6C, an alternative embodiment of second portion 30' is shown. Second portion 30' includes a substantially flat surface 32, an outer perimeter 34, and an inner perimeter 35 defining a central opening 36. Second portion 30' further includes a rim 40, projecting inwardly from, and extending around a section of, outer perimeter 34. Rim 40 forms a second channel 42 to oppose first channel 20, such that second portion 30 is slidable relative to first portion 12. As noted, alternative embodiment of second portion 30' includes each element of the embodiment described in and shown in FIGS. 5A, 5B and 5C. In addition, however, second portion 30' includes tab portion 44, including slots 45 for receipt of a connecting means (not shown). The connecting means can be a band, string, crown strap, or the like, to keep a pair of second portions 30' together for the user to readily locate and install on first portion 12, as noted above. Tab portion 44 may also be used as a grip for the user to pull or slide second portion 30' off of first portion 12 when replacing a soft sealing element, or to slide a new soft sealing element onto first portion 12.

The present invention will be further illustrated by the following example, which is intended to be illustrative in nature and is not to be construed as limiting the scope of the invention.

EXAMPLE

One suitable construction of a seal plate attachment for an earmuff having a shape and design substantially in accordance with the present invention is provided by the following combination of elements.

A polyvinyl chloride seal plate attachment for earmuffs was molded by standard injection molding techniques. The seal plate attachment includes first and second portions having substantially flat top surfaces, outer perimeters and central openings.

The first portion is generally rectangular in shape with rounded corners. The first portion has a length of 3.70 inches and a width of 2.70 inches, at the outer perimeter. The first portion's ovular central opening, defined by the first portion's inner perimeter, has a length of 2.7 inches and a width of 1.7 inches, thereby providing a continuous flange-like surface having a width of 0.50 inch. The first portion is approximately 0.13 inch thick, and includes a projection on its underside, which extends below the substantially flat surface and is parallel to the outer perimeter. The projection is set-in from the outer perimeter of the first portion approximately 0.10 inch, and is approximately 0.10 inch thick and about 0.17 inch long. The projection is shaped and sized to allow the first portion to be snapped into, or be adhesively bonded to, a rigid earmuff cup having a similar outer perimeter shape and a wall thickness of about 0.10 inch.

The first portion of the seal plate attachment includes a first channel extending around a section of the outer perimeter. The channel is formed on three sides of the rectangular shaped first portion. The top surface of the channel is set in 0.10 inch from the outer perimeter, and the channel's groove extends into the first portion an additional 0.10 inch. The top channel surface, and the channel itself, are approximately 0.04 inch thick, while the base of the channel is approximately 0.05 inch thick. Lastly, a 2° interface was measured between the inner and outer perimeters of the first portion.

The seal plate attachment second portion is shaped and sized similarly to the first portion, as described above. The second portion is generally rectangular shaped with rounded corners and has outer perimeter dimensions including a 3.7 inch length and a 2.7 inch width, as well as an ovular central opening, defined by the second portion's inner perimeter, having a 2.7 inch length and a 1.7 inch width. The second portion includes a rim, projecting inwardly from and extending around a section of the outer perimeter. The rim is approximately 0.20 inch wide, and extends around the same three sides as the first channel of the first portion (described above). A second channel, opposing the first channel in the first portion, is formed in the rim having a depth of approximately 0.10 inch. The top surface of the rim is approximately 0.04 inch thick while the second channel thickness is approximately 0.50 inch. The second portion has a thickness of 0.04 inch. The second channel formed in the rim, opposing the first channel of the first portion, allows the second portion to be slidable relative to the first portion. The first channel forms a track for the second channel, as the second portion is slid onto and over the first portion to completely cover its substantially flat surface.

A lip is provided on both the outer perimeter and inner perimeter (surrounding the central opening) of the substantially flat surface of the second portion. Both lips have a height and width of 0.02 inches. The lip provides a border for a soft sealing element which can be adhesively bonded, or attached by other means known to those of skill in the art, to the substantially flat surface of the second portion. Several different types and sizes of a soft sealing element can be provided and attached to many seal plate attachment second portions, allowing users to interchange soft sealing elements as desired by simply sliding the desired soft sealing element into place on the first portion, and sliding it off for replacement or disposal.

Although particular embodiments of the invention have been described in detail for purposes of illustration, various modifications may be made without departing from the spirit and scope of the invention.

What is claimed is:

1. A seal plate attachment for earmuffs, comprising:
   a first portion having a substantially flat surface, an outer perimeter and an inner perimeter defining a central opening,
   said first portion including a first channel extending around a section of said outer perimeter; and
   a second portion having a substantially flat surface, an outer perimeter and an inner perimeter defining a central opening,
   said second portion including a rim projecting inwardly from and extending around a section of said outer perimeter,
   said rim forming a second channel to oppose said first channel, such that said second portion is slidable relative to said first portion,
   wherein a soft sealing element is attached to said second portion flat surface.

2. The seal plate attachment of claim 1 wherein said first and second portions are substantially the same size and shape.

3. The seal plate attachment of claim 1 wherein said first and second channels extend around substantially equivalent outer perimeter sections of said first and second portions.

4. The seal plate attachment of claim 3 wherein said first and second channels continuously extend around at least 50% of said first and second portion outer perimeters.

5. The seal plate attachment of claim 1 wherein said soft sealing element is a foam material having a low static stiffness and a high dynamic stiffness.

6. The seal plate attachment of claim 1 wherein said first and second portions are constructed of a semi-rigid material.

7. The seal plate attachment of claim 6 wherein said first and second portions are constructed of a semi-rigid plastic.

8. The seal plate attachment of claim 1 wherein said first portion is constructed of a rigid material.

9. The seal plate attachment of claim 8 wherein said first portion is constructed of a rigid plastic.

10. The seal plate attachment of claim 9 wherein said first portion is constructed of a material selected from the group consisting of: high-density polyethylene, acrylonitrile-butadiene-styrene resin, polypropylene, polycarbonate, polyvinyl chloride, and nylon.

11. The seal plate attachment of claim 1 wherein said second portion includes a tab portion for receipt of a connecting means.

12. An earmuff comprising:
    a pair of rigid earcup elements;
    a connecting band attached to each of said earcup elements;
    a pair of seal plate attachments, each of said attachments having first and second portions including substantially flat surfaces, outer perimeters, and inner perimeters defining central openings,
    said seal plate attachment first portion including a first channel extending around a section of said outer perimeter,
    said seal plate attachment second portion including a rim, projecting inwardly from and extending around a section of said outer perimeter,
    said rim forming a second channel to oppose said first channel, such that said second portion is slidable relative to said first portion; and
    a pair of soft sealing elements, each attached to said flat surface of said seal plate attachment second portion.

13. The earmuff of claim 12 wherein said seal plate attachment first portion is demountably attached to said rigid earcup element.

14. The earmuff of claim 12 wherein said seal plate attachment first portion is integral with said rigid earcup element.

15. The earmuff of claim 12 wherein said seal plate attachment first and second portions are substantially the same size and shape.

16. The earmuff of claim 12 wherein said seal plate attachment first channel and rim extend around substantially equivalent sections of said first and second portion perimeters.

17. The earmuff of claim 16 wherein said seal plate attachment first channel and rim extend around at least 50% of said first and second portion perimeters.

18. The earmuff of claim 12 wherein said soft sealing elements are constructed of a foam material having a low static stiffness and a high dynamic stiffness.

19. The earmuff of claim 12 wherein said seal plate attachment first and second portions are constructed of a semi-rigid plastic material.

20. The earmuff of claim 12 wherein said seal plate attachment first portion is constructed of a rigid plastic material.

21. The earmuff of claim 20 wherein said seal plate attachment first portion is constructed of a material from the group consisting of: high-density polyethylene, acrylonitrile-butadiene-styrene resin, polypropylene, polycarbonate, polyvinyl chloride, and nylon.

22. The earmuff of claim 12 wherein said seal plate attachment second portion includes a tab portion for receipt of a connecting strap.

* * * * *